United States Patent [19]

Cardin et al.

[11] Patent Number: 5,447,911
[45] Date of Patent: Sep. 5, 1995

[54] **GHILANTEN ANTIMETASTATIC PRINCIPLE FROM THE SOUTH AMERICAN LEECH, *HAEMENTERIA GHILIANII***

[75] Inventors: Alan D. Cardin; Sai P. Sunkara, both of Cincinnati, Ohio

[73] Assignee: Merrell Dow Pharmaceuticals Inc., Cincinnati, Ohio

[21] Appl. No.: 224,096

[22] Filed: Apr. 6, 1994

Related U.S. Application Data

[63] Continuation of Ser. No. 975,259, Dec. 19, 1991, abandoned, which is a continuation of Ser. No. 438,365, Dec. 14, 1989, abandoned, which is a continuation-in-part of Ser. No. 368,616, Jun. 20, 1989, abandoned.

[51] Int. Cl.$^6$ ..................... A61K 38/58; A61K 38/17
[52] U.S. Cl. ......................................... 514/12; 514/21; 530/856; 530/858
[58] Field of Search .................... 514/12, 21; 530/858, 530/856

[56] References Cited

U.S. PATENT DOCUMENTS

| | | | |
|---|---|---|---|
| 4,390,630 | 6/1983 | Sawyer et al. | 435/219 X |
| 4,588,587 | 5/1986 | Gasic | 514/21 X |
| 4,832,849 | 5/1989 | Cardin | 514/21 X |

FOREIGN PATENT DOCUMENTS 0263608  4/1988  European Pat. Off. .

OTHER PUBLICATIONS

Gasic et al., Cancer Research, 43, 1633–1636 (1983).
J. of the International Society on Thrombosis & Hamosteasis, 61(3), 437–441 (1989), Condra et al.
J. of Biological Chemistry, vol. 262, No. 20, 9718–9723, Tuszynski et al.
G. J. Gasic et al., Proceedings of the American Association for Cancer Research, Los Angeles, Calif., 7–10 May 1987, vol. 27, p. 66, Abstract No. 261.
Brankamp, et al., *Ghilantens: Anticoagulant-antimetastatic proteins from the South American leech, Haementeria ghilianii*, J. Lab Clin. Med., vol. 115(1), (Jan. 1990).
Blankenship, et al. *Biochem. and Biophysical Research Communications, Amino Acid Sequence of Ghilanten: Anticoagulant-Antimetastatic Principle of the South American Leech, Haementeria Ghilianii*, vol. 166(3), 1384–1389, (Feb. 14, 1990).
Brankamp, et al., *Biochem. and Biophysical Research Communications, Demonstration That [$A^{103,106,108}$] Antistasin 93–119 Inhibits the Specific Binding of Antistasin to Sulfatide [Gal(3-SO4)$\beta$1-1Cer]*, vol. 181(1), 246–251, (Nov. 27, 1991).
Brankamp, et al., *Blood Coagulation and Fibrinolysis, Studies on the anticoagulant, antimetastatic and heparin-binding properties of ghilanten-related inhibitors*, vol. 2, 161–166 (1991).

*Primary Examiner*—Howard E. Schain
*Attorney, Agent, or Firm*—Kenneth J. Collier

[57] ABSTRACT

A method for the inhibition of tumor metastases is described herein. The method makes use of the administration of an antimetastatic factor isolated from the leech *Haementeria ghilianii*.

6 Claims, 12 Drawing Sheets ghilanten

C  V

GHILANTEN ANTIMETASTATIC PRINCIPLE FROM THE SOUTH AMERICAN LEECH, *HAEMENTERIA GHILIANII*

CROSS-REFERENCE TO RELATED APPLICATION

This is a continuation of application Ser. No. 07/975,259, filed Dec. 19, 1991, now abandoned, which is a continuation of application Ser. No. 07/438,365, filed Dec. 14, 1989 now abandoned; which is a continuation-in-part of application Ser. No. 07/368,616, filed Jun. 20, 1989, now abandoned, which is herein incorporated by reference.

FIELD OF INVENTION

This invention relates to the discovery that the proteinaceous substance having Factor $X_a$ inhibition activity isolated from the saliva or salivary glands of the leech *Haementeria ghilianii* possesses antimetastatic activity.

BACKGROUND OF INVENTION

The spread of cancer cells from a primary tumor site to distant organs is known as metastasis. Metastasis has been considered one of the most intriguing aspects of the pathogenesis of cancer. This is certainly true to the extent that cancer tumor metastasis is responsible for most therapeutic failures when the disease is treated, as patients succumb to the multiple tumor growth. The extent to which metastasis occurs varies with the individual type of tumor. Melanoma, breast cancer, lung cancer and prostate cancer are particularly prone to metastasize.

When metastasis takes place, the secondary tumors can form at a variety of sites in the body, with one of the more common sites for metastasis being the lung.

Thus, inhibition of tumor metastasis to any extent would be beneficial and this would be true regardless of whether the agent involved in the inhibition had any effect on the primary tumor. Of course, if the agent also inhibited the primary tumor, this would be an additional advantage for the agent.

Leeches have been used medicinally since antiquity. The medicinal use of leeches in the early 19th century, caused the near extinction of the species *Hirudo medicinalis* and caused Russia to impose quotas of its export. More recently, leech secretions have been more scientifically studied and have been found to contain a variety of biological products having a wide spectrum of biochemical and pharmacological activities such as anticoagulant, antimetastatic, anaesthetic, antibiotic, and vasodilator. For example, Hirudin isolated from the salivary gland of the leech *Hirudo medicinalis* is the most specific and potent thrombin inhibitor known. Further, hementin which is isolated from the salivary gland of the leech *Haementeria ghilianii* is a fibrin(ogen)olytic enzyme of, reported high molecular weight. It is reportedly the anticoagulant principle of this leech. This enzyme degrades fibrinogen and fibrin rather than activating the host fibrinolytic system or inhibiting the coagulation system.

Applicants have discovered that the proteinaceous substance having anticoagulant activity isolated from the saliva or salivary glands of the leech *Haementeria ghilianii* also possesses valuable and useful antimetastatic activity.

SUMMARY OF THE INVENTION

The proteinaceous substance having Factor $X_a$ inhibiting activity originating from the salivary gland of the leech *Haementeria ghilianii* and isolated therefrom is a useful antimetastatic agent and is henceforth referred to as ghilanten. The name ghilanten shows that this proteinaceous substance originates from *Haementeria ghilianii* (ghil-) and anti factor $X_a$ (-anten) activity. This antimetastatic factor is isolated by subjecting the leech saliva or salivary gland extract of the leech *Haementeria ghilianii* to chromatographic separation using an anionic exchange resin and eluting with an increasing salt gradient. Those fractions having high Factor $X_a$ inhibiting activity and anticoagulant activity are then subjected to reverse phase high pressure liquid chromatography (HPLC) to purify further the substance having Factor $X_a$ inhibiting and antimetastatic activity.

More specifically, the present invention relates to a method for inhibiting the formation of tumor metastases comprising the administration of an amount, which is safe and sufficient to inhibit the formation of tumor metastases, of the antimetastatic factor ghilanten which is a proteinaceous substance isolated from the saliva of *Haementeria ghilianii*, to a patient having melanoma, breast cancer, lung cancer or prostate cancer.

DETAILED DESCRIPTION OF TEE INVENTION

Figure 1A:
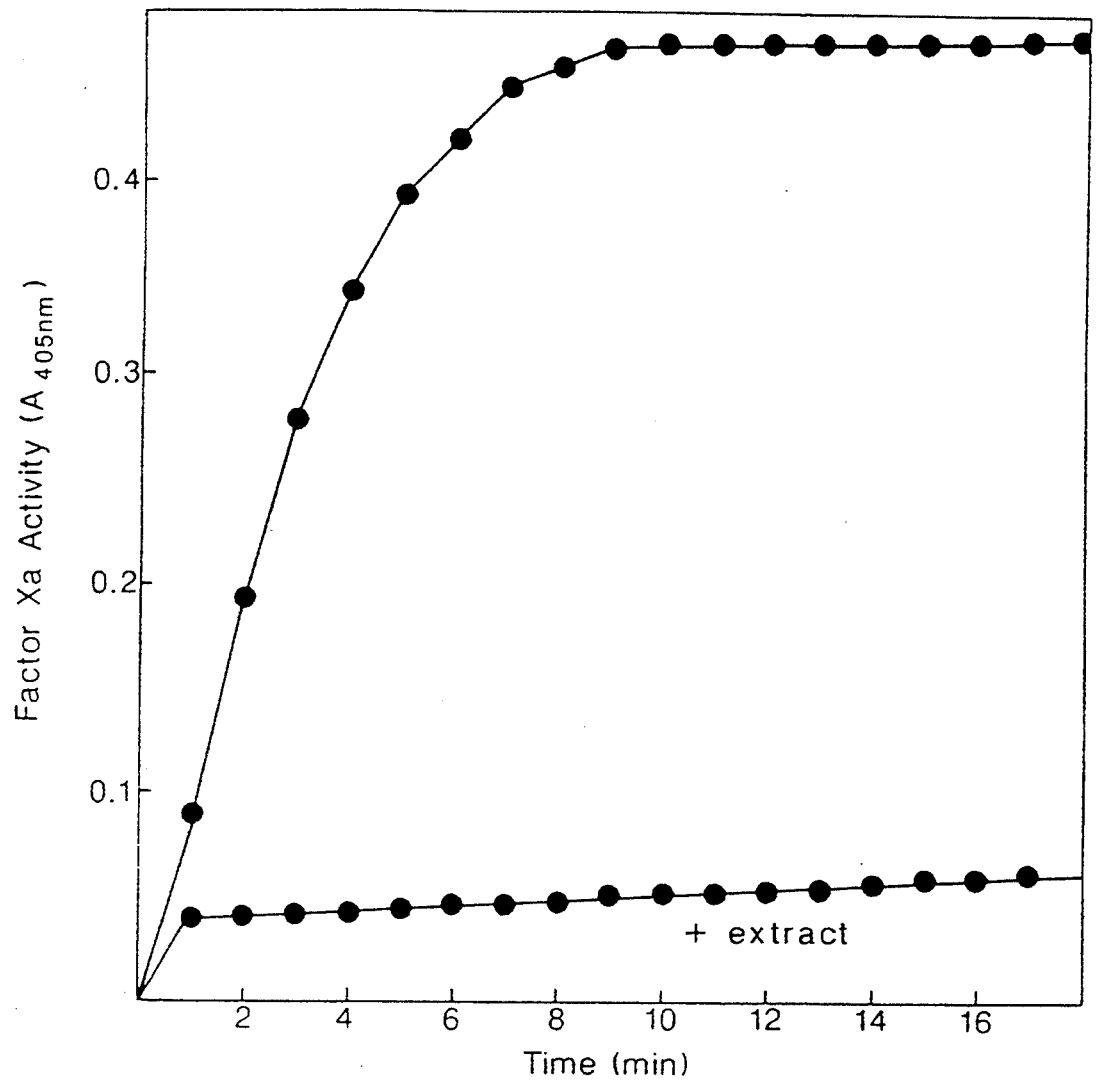
FIG. 1. Inhibition of $FX_a$ by crude salivary gland extract of *Haementeria ghilianii*. Approximately 11 μg of salivary gland extract (soluble protein) were added to 16 ng of purified $FX_a$. The sample was incubated for 10 minutes at room temperature and the amidolytic activity determined after the addition of methoxycarbonyl-D-cyclohexylglycyl-glycyl-arginine-p-nitroanilide acetate; p-nitroaniline formation was monitored spectophotometrically at 1 minute interval recordings at 405 ηm. Top curve: bovine $FX_a$ and chromogenic substrate; bottom curve: bovine $FX_a$, salivary gland extract and chromogenic substrate. Inset: (top curve) human $FX_a$ and chromogenic substrate: (bottom curve) human $FX_a$, salivary gland extract and chromogenic substrate. Salivary gland extract of *H. ghilianii* did not inhibit the hydrolysis of H-D-hexahydrotyrosyl-L-alanyl-L-arginine-p-nitroanilide acetate by bovine and human thrombins (not shown).

The term saliva as used herein includes not only saliva (or salivary secretions) but homogenized tissue from the whole leech as well as any part of the leech, particularly the salivary glands. The term saliva includes, as well, any isolate of the saliva so long as, of course, the isolate or tissue homogenate contains the antimetastatic factor of this invention having Factor $X_a$ inhibiting activity.

The antimetastatic factor of this invention having Factor $X_a$ inhibiting and antimetastatic activity is comprised of several sequence related proteins with Factor $X_a$ inhibiting and antimetastatic activity. For the purposes of this invention, all the proteins/peptides having substantial Factor $X_a$ inhibiting and antimetastatic activity, that is, having an $IC_{50}$ with respect to Factor $X_a$ of at least 1000 nM, individually and in combinations, from the saliva of the leech *Haementeria ghilianii*, are intended. Applicant specifically intends that the antimetastatic factor of this invention include such substance however derived whether through sequential and block synthesis or through gene cloning, including synthetic gene construction, and expression.

While the complete amino acid sequence of the antimetastatic factor is not yet completely known, the substantially complete sequence of one of the proteins is as follows:

Pyr-Glu-Gly-Pro-Phe-Gly-Pro-Gly-Cys-Glu-Glu-Ala-Gly-Cys-Pro-Glu-Gly-Ser-Ala-Cys-Asn-Ile-Ile-Thr-Asp-Arg-Cys-Thr-Cys-Pro-Glu-Val-Arg-Cys-Arg-Val-Tyr-Cys-Ser-His-Gly-Phe-Gln-Arg-Ser-Arg-Tyr-Gly-Cys-Glu-Val-Cys-Arg-Cys-Arg-Thr-Glu-Pro-Met-Lys-Ala-Thr-Cys-Asp-Ile-Ser-Glu-Cys-Pro-Glu-Gly-Met-Met-Cys-Ser-Arg-Leu-Thr-Asn-Lys-Cys-Asp-Cys-Lys-Ile-Asp-Ile-Asn-Cys-Arg-Lys-Thr-Cys-Pro-Asn-Gly-Leu-Lys-Arg-Asp-Lys-Leu-Gly-Cys-Glu-Tyr-Cys-Glu-Cys-Lys-Pro-Lys-Arg-Lys-Leu-Val-Pro-Arg-Leu-Ser.

Additionally, it is known that the peptides comprising the antimetastatic factor of this invention have a molecular weight of about 18 kdal and are not highly glycosylated. While some sugar groups may be present, applicant has found that apparent molecular weight does not vary significantly with polyacrylamide gel concentration in the SDS PAGE determination, suggesting lack of significant glycosyl groups on the peptides. Applicant has also found that each peptide has about 3 alanine residues, 3 methionine residues, 7–9 lysine residues, 9–10 arginine residues, and 8–9 proline residues and a low abundancy of aromatic residues, such as, 3 phenylalanine and 3 tyrosyl residues, when amino acid analysis is performed. More precise composition information, such as the number of cysteine/cystine and tryptophan residues, awaits availability of larger quantities of peptide and completion of sequence analysis.

The following common abbreviations of the amino acids are used throughout this specification:

Ala (or A)—alanine
Arg (or R)—arginine
Asx—asparagine (N) (Asn) and/or aspartic acid (D) (Asp)
Cys (or C)—cysteine
Gly (or G)—glycine
Glx—glutamine acid (E) (Glu) and/or glutamine (Q) (Gln)
His (or H)—histidine
Ile (or I)—isoleucine
Leu (or L)—leucine
Lys (or K)—lysine
Met (or M)—methionine
Phe (or F)—phenylalanine
Pro (or P)—proline
Set (or S)—serine
Thr (or T)—threonine Tyr (or Y)—tyrosine
Val (or V)—valine The antimetastatic factor of this invention can, like many proteins/peptides, form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

The experiments below demonstrate the ability of the proteinaceous substance isolated from the leech *Haementeria ghilianii* or its compositions to inhibit metastasis of tumor cells and, particularly, metastasis of tumor cells to lungs. The lungs provide a convenient organ for the study of metastasis in the animal body. The effect of the antimetastatic factor of this invention on certain tumor cells is also demonstrated below.

To confirm the anti-metastatic activity of the proteinaceous substances of this invention, $1 \times 10^5$ viable B16 melanoma F10 line cells were injected i.v. through the tail vein of C57/BL mice. The antimetastatic factor was then administered i.v. at −2, +2, +4 and +6 hours relative to the tumor innoculum at t=0 hours. At the end of 15 days, the animals were sacrificed and the number of metastatic foci in the lungs were quantitated. The results observed are summarized in Table 1 below, with n indicating the number of animals used in the test.

TABLE 1

ANTIMETASTATIC ACTIVITY OF HIRUDIN AND FACTOR Xa INHIBITOR FROM (GHILANTEN) *HAEMENTERIA GHILIANII*

| Treatment | No. of Metastatic Foci (Mean + S.E.; n = 6) | % Inhibition | % Potentiation |
|---|---|---|---|
| Vehicle Control | 163 ± 9 | — | — |
| Hirudin | 198 ± 10 | 0 | 21 |
| Ghilanten | *110 ± 8 | 33* | 0 |

*Significant at p < 0.02 compared to control
Significant at p < 0.05
B16 melanoma F10 cells (1 × 105 cells/animal) were injected i.v. into the tail vein of C57/Bl mice on day 0. Vehicle: 10 mM Hepes, 0.15M NaCl, pH 7.4 containing 10 mg/ml BSA; recombinant-Hirudin (25 antithrombin units) and FXa inhibitor (1–2 μg) were injected into the mice i.v. at −2, +2, +4, +6 hrs. after tumor cell innoculation. The animals were sacrificed at 14 days post tumor cell innoculation. The lungs were dissected, fixed, and the number of pulmonary metastases were determined under a dissecting microscope.

TABLE 2

EFFECT OF HIGHER DOSE GILANTEN ON METASTASES OF B16F10 MELANOMA CELLS IN C57/BL MICE

| Treatment | No. of Metastatic Foci | % Inhibition |
|---|---|---|
| Vehicle Control | *99 ± 28 (n = 3) | 0 |
| Ghilanten | **20 ± 6 (n = 2) | 80 |

*Mean + S.E.
**Average foci values of 15 and 26.
In this experiment, ghilanten (5 μg) was injected into the mice i.v. at −2, +2 and +4 hours relative to tumor cell innoculation. Experimental conditions are the same as described in Table 1.

It should be evident from the results in the above table that the antimetastatic factor significantly inhibited metastasis in the animals after a single daily treatment when administered −2, +2, +4 and +6 hours relative to the tumor cell innoculation at time=0 hours. Moreover, this antimetastatic factor is as highly specific in its action as hirudin, a potent thrombin inhibitor, and caused a moderate increase in metastatic foci.

The method of treatment by inhibition of metastasis disclosed and claimed herein may be used alone or in combination as part of a treatment regimen for an animal or human patient having a cancer that is prone to metastasis, particularly, melanoma, breast cancer, lung cancer and prostate cancer. The treatment to inhibit the formation of metastases is best administered as soon after the detection of the cancer as possible. By utilizing the treatment regimen in patients at an early stage, the treating physician maximizes the chances that significant metastasis has not yet occurred. This maximizes chances for successful treatment. In such a regimen, the antimetastatic factor or its salts may, and generally will, be administered in combination with another form of therapy which controls the primary tumor itself. The other therapy in such a combination can include, but is not limited to, radiation therapy or the administration of compatible antitumor or antineoplastic agents. Examples of such antineoplastic agents include melphalan, lomustine capsules, cyclophosphamide, fluorouracil and also ornithine decarboxylase inhibitors such as difluoromethylornithine (DFMO), 6-heptyne-2,5-diamine and (E)-2,5-diamino-2-(fluoromethyl)-3-pentenoic acid methyl ester dihydrochloride. The treatment described in the present application may also be used conjointly with (i.e., either preceding or subsequent to) a surgical procedure to remove the primary tumorous material from the body. Frequently, surgical procedures to remove tumorous material from the body are avoided because of the fear that metastasis of tumor cells will occur as a result of the physical manipulation involved. However, if the antimetastatic factor of this invention or its salts are administered to the patient prior to the surgical procedure, then the risk of metastasis which may result from surgery can be reduced and surgery would be a more attractive treatment option.

Within the scope of sound medical judgement, the dosage of antimetastatic factor or its salts and the method of administration used in the present invention will vary with the severity and nature of the particular condition being treated, the duration of treatment, the adjunct therapy used, the age and physical condition of the patient, and like factors within the specific knowledge and expertise of the attending physician. However, single dosages can typically range from 0.01 to 2000 milligrams per kilogram of body weight, preferably 1 to 200 milligrams per kilogram (unless otherwise specified, the unit designated "mg/kg", as used herein, refers to milligrams per kilogram of body weight). Up to four doses per day can be used routinely, but this can be varied according to the needs of the patient, consistent with a sound benefit/risk ratio. Variation in patient response may be expected but the higher dosages within the ranges indicated are usually required in the case of oral administration while the lower dosages indicated would apply for intravenous administration.

For purposes of oral administration, the antimetastatic factor or its salts can be formulated in the form of capsules, tablets or granules while for intravenous administration, the active material can be formulated in an appropriate solution. In any case, the active compound is mixed with an appropriate pharmaceutical carrier.

Although the antimetastatic factor of this invention may survive passage through the gut following oral administration, applicants prefer non-oral administration, for example, subcutaneous, intravenous, intramuscular or intraperitoneal; administration by depot injection; or by implant preparation.

For parenteral administration the antimetastatic substance of this invention may be administered as injectable dosages of a solution or suspension of the substance in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The antimetastatic factor of this invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The antimetastatic factor of this invention is prepared from leech saliva. Saliva gland extract from either the anterior or posterior salivary glands of *H. ghilianii*, or both, for use in obtaining and purifying the antimetastatic factor of this invention can be obtained in several ways, such as surgical removal of the glands and homogenation, extracting tissue homogenate with, for example, ammonium sulphate solution or other salts, such as sodium chloride or buffers, or with acetone and concentrating or dehydrating the extract, or by ultracentrifugation of the tissue homogenate. The resulting crude salivary gland extract is then subjected to conventional chromatography in order to isolate that portion having anti-$FX_a$ and anticoagulant activities. Applicant has employed chromatography on DEAE-cellulose, an anionic exchange resin and on a heparin-agarose resin eluting with a linear, increasing salt gradient of sodium chloride. Other resins can, of course, be substituted and elution with other salts with various gradients or with organic solvents or mixtures and using varying column flow rates isolating that portion having Factor $X_a$ inhibiting and anticoagulant in the usual manner.

The resulting purified salivary gland extract is then subjected to an affinity chromatography step using Factor $X_a$, such as bovine Factor $X_a$, bound to a chromatography resin, such as those resins typically used in affinity chromatography having chemical groups available for binding Factor $X_a$. Applicant has used Affi-Gel-15, a N-succimidyl ester containing resin available from Bio-Rad Corporation. With this resin, Factor $X_a$ can be bound by incubating the resin together with the Factor $X_a$ with 4-morpholinopropanesulfonic acid and subsequently with ethanolamine. The purified salivary gland extract is chromatographed using this resin eluting with HEPES, 4-(2-hydroxyethyl)-1-piperazineethanesulfonic acid, containing the active site reversible serine protease inhibitor, benzamidine, and collecting that portion having anticoagulant and amidolytic activity. Benzamidine is easily removed by dialysis or subsequent chromatography steps. Various conventional variations on this affinity chromatography technique will be readily apparent to those skilled in the art.

The resulting crude proteinaceous substance having Factor $X_a$ inhibiting activity is then further purified. This purification can be accomplished in any conventional manner such as by reverse phase chromatography, a type of chromatography in which the stationary phase is nonpolar and the eluting phase is polar. The stationary phase is typically a hydrocarbon chain chemically bonded to an inert surface, such as glass and the eluting phase is aqueous methanol, acetonitrile or propanol. In the case of hydrophobic interaction chromatography the stationary phase is non-polar and the eluting phase is polar, such as water or aqueous buffer. Applicant has used a C-18 type resin, that is, a resin wherein the hydrocarbon bound to the solid resin is substantially 18 carbon containing hydrocarbon, such as the Aquapore RP-300, C-18 resin eluting with a linear, increasing gradient of aqueous acetonitrile containing trifluoroacetic acid. However, other suitable columns may include $C_3$, $C_4$, $C_6$, $C_8$, etc.

EXAMPLES

This invention is illustrated by the following, nonlimiting examples.

EXAMPLE 1

Preparation of ghilanten, $FX_a$ inhibiting substance from *H. Ghilianii* salivary gland extract and characterization Coagulation, Chromogenic and Fibrin(ogen)olytic Assays Prothrombin times were determined as one-stage clotting assays with an Electra 800 automatic coagulation timer (Medical Laboratory Automation, Inc.), using the standard programs and reagents recommended by the manufacturer. Briefly, various amounts of either (i) a crude extract of the salivary gland tissue from *Haementeria ghilianii* in 20 mM HEPES, 0.15M NaCl, 2.5 mM $CaCl_2$, pH 7.4 (ii) chromatographic fractions of *H. ghilianii* salivary gland extract in column elution buffer or (iii) purified FXa inhibitor (ghilanten) from *H. ghilianii* salivary glands in 20 mM HEPES, 0.15M NaCl, 2.5 mM $CaCl_2$, pH 7.4 were added to 100 $\mu$l of citrated normal human plasma. Clot times were determined following the addition of 200 $\mu$l of thromboplastin reagent (DADE®) containing 11.6 mM $CaCl_2$. Chromogenic assays of $FX_a$ and thrombin amidolytic activities were performed in 96 well microtitre plates (Accurate Chemical and Scientific Corp., Westbury, N.Y.) with methoxycarbonyl-D-cyclohexylglycyl-glycyl-arginine-p-nitroanilide acetate and H-D-hexahydrotyrosyl-L-alanyl-L-arginine-p-nitroanilide acetate, respectively. In these assays, from 0.15 to 350 ng of enzyme in 25 μl of 20 mM HEPES, 0.15M NaCl, pH 7.4 (assay buffer) were added to 25 μl of assay buffer followed by the addition of 50 μl of the appropriate inhibitor sample. The solutions were incubated 10 minutes at room temperature and the assay started by the addition of 100 μl of chromogenic substrates at a final concentration of $2.5 \times 10^{-4}$M. The amidolytic activities in the absence and presence of inhibitor were monitored spectrophotometrically at 405 nm for p-nitroaniline absorbance with an EL309 Microplate Autoreader (BIO-TEK Instruments) at 1 minute interval recordings.

$^{125}$I-labeled (human) fibrinogen was prepared as described by Knight, et al., Thromb. Haemostas (Stuttgart) 46, 593–596 (1981). Fibrinogen (5 mg) in 5 ml of 50 mM Tris-HCl, 0.1M NaCl, 0.025M sodium citrate, pH 7.9 were mixed with 500 μCi of Na$^{125}$I (New England Nuclear, Boston, Mass.) with 5 μl of 0.045% NaI carrier in a plastic culture tube and chilled on ice. To initiate the reaction, the mixture was transferred to a chilled tube coated with 100 μg of iodogen and stirred gently in an ice bath for 1 hour. To stop the radioiodination reaction, the protein solution was decanted into a plastic culture tube to separate iodogen from the reactants. BSA (5 mg) was then added to the sample and the solution was then fractionated on a 0.5×12 ml column of BioGel P-2 equilibrated in 0.05M Tris-HCl, 0.1M NaCl, pH 7.9 to separate any remaining free $^{125}$I from $^{125}$I-labeled-fibrinogen. The specific radioactivity is $1.9 \times 10^8$ dpm/mg.

The fibrinogenolytic assay was based on the ability of hementin (S. M. Malinconico, et al., J. Lab. Clin. Med. 103, 44–58 (1984)) in chromatographic fractions to degrade $^{125}$I-labeled fibrinogen to trichloroacetic acid soluble $^{125}$I-labeled peptides. In this assay 100 μl of the DEAE-5PW chromatographic fractions were incubated with 50 μg of $^{125}$-labeled fibrinogen in 227 μl of 50 mM Tris-HCl, 0.1M NaCl, pH 7.9; the sample was adjusted to 10 mM in CaCl$_2$ and then incubated overnight at 37° C. To this was added 100 μl of BSA (3 mg/ml) in incubation buffer followed by the addition of 427 μl of ice cold 20% trichloroacetic acid (TCA). The samples were placed on ice for 2 hours, subjected to centrifugation and the radioactivity in the pellets and supernatants were determined by gamma counting. Fibrinogenolytic activity is expressed as the ratio of the TCA soluble counts to the TCA insoluble counts (TCA sol/TCA ppt).

Preparation of Salivary Gland Extract

Salivary glands of H. ghilianii, corresponding to a hementin activity of 50 units/mg protein (S. M. Malinconico, et al., J. Lab. Clin. Med. 103, 44–58 (1984)) were macerated with a glass rod in a 3 ml glass Reacti-Vial (Pierce Chemical Co.) containing 2 ml of 20 mM HEPES, pH 7.8 (extraction buffer). The vial was placed on ice and the contents subjected to microprobe tip sonication (Branson Sonic Power Supply) with four 30 second power bursts using a 30% duty cycle and power level 3. The vial was centrifuged for 5 minutes at 3750 rpm, the supernatant collected and then recentrifuged at 8500 rpm on an Eppendorf tabletop centrifuge. The pellet from the first centrifugation step was resuspended in 2 ml of extraction buffer and the above procedure repeated. The supernatants resulting from the two sonication extractions were then combined and used immediately for purification.

Preparation of Bovine FX$_a$-Affi-Gel-15 Affinity Matrix

Bovine FX$_a$ was coupled to Affi-Gel-15 by incubation of 2 mg of purified enzyme in 2 ml of 4-morpholinopropanesulfonic acid (MOPS), pH 7.5 (coupling buffer) with 2.5 ml of resin at 4° C. overnight. The beads were extensively washed and then resuspended in 3 ml of coupling buffer. The beads were next reacted with 0.3 ml of 1M ethanolamine, pH 8.0 overnight at 4° C. and then washed extensively with 0.05M HEPES, 0.1M NaCl, pH 7.5 containing 0.1% Tween-20.

Purification of FX$_a$ Anticoagulant

Figure 3:
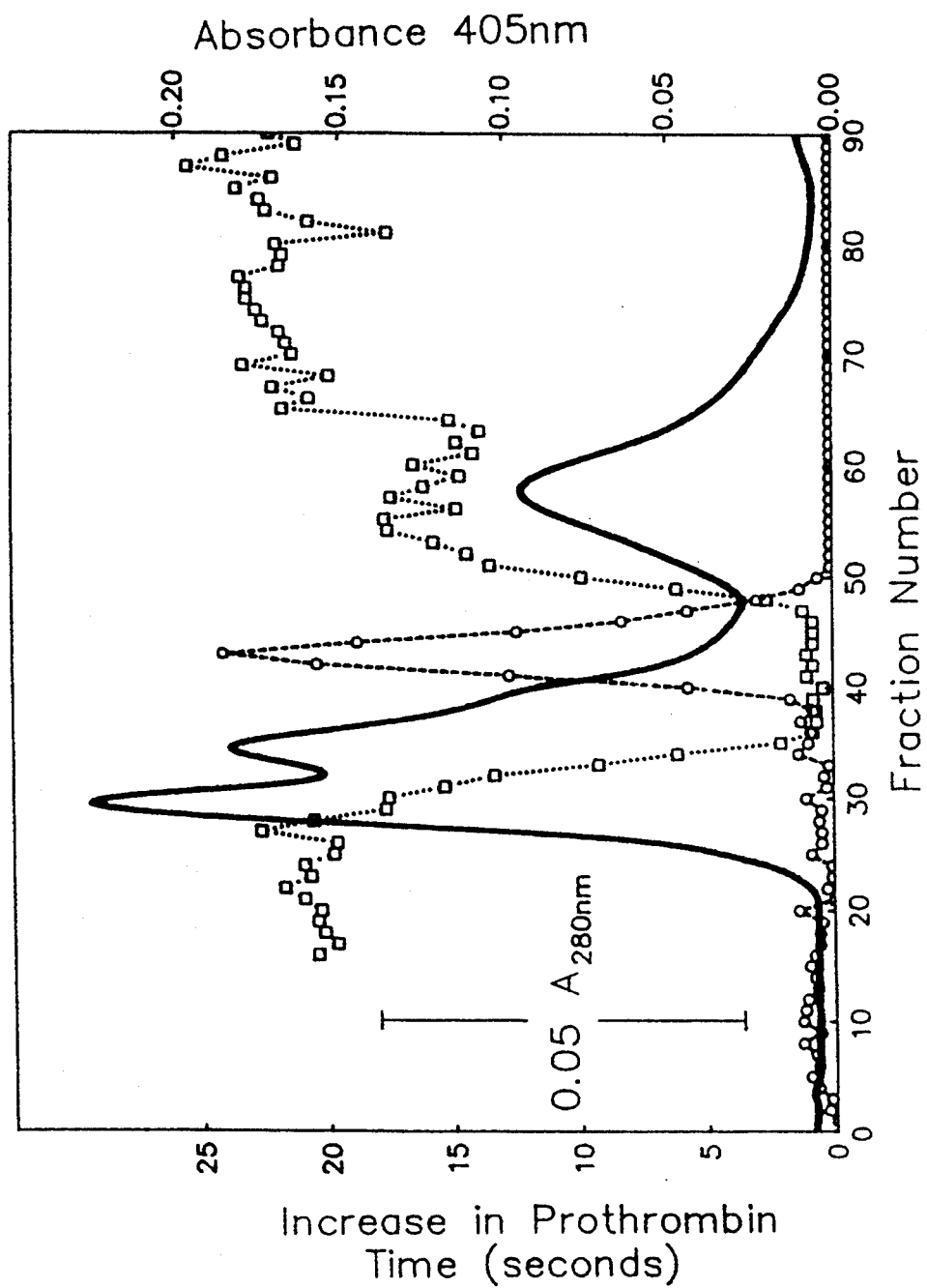
FIG. 3. Fractionation of the partially purified $FX_a$ inhibitor by heparin agarose chromatography. The DEAE fractions with coeluting anticoagulant and anti-$FX_a$ activities were pooled and loaded onto a 0.5×5 cm column of heparin agarose. Proteins were eluted with a linear gradient of NaCl to 1M in 20 mM HEPES, pH 7.8. The flow rate was 1 ml/minute and 1 ml fractions were collected. Anticoagulant activity (open circle) was determined by a one-stage clot assay as the prolongation in prothrombin time. Inhibition of $FX_a$ was measured at 405 nm for inhibition of p-nitroaniline formation (open square) using the chromogenic substrate methoxycarbonyl-D-cyclohexylglycyl-glycyl-arginine-p-nitroanilide acetate.
Figure 4:
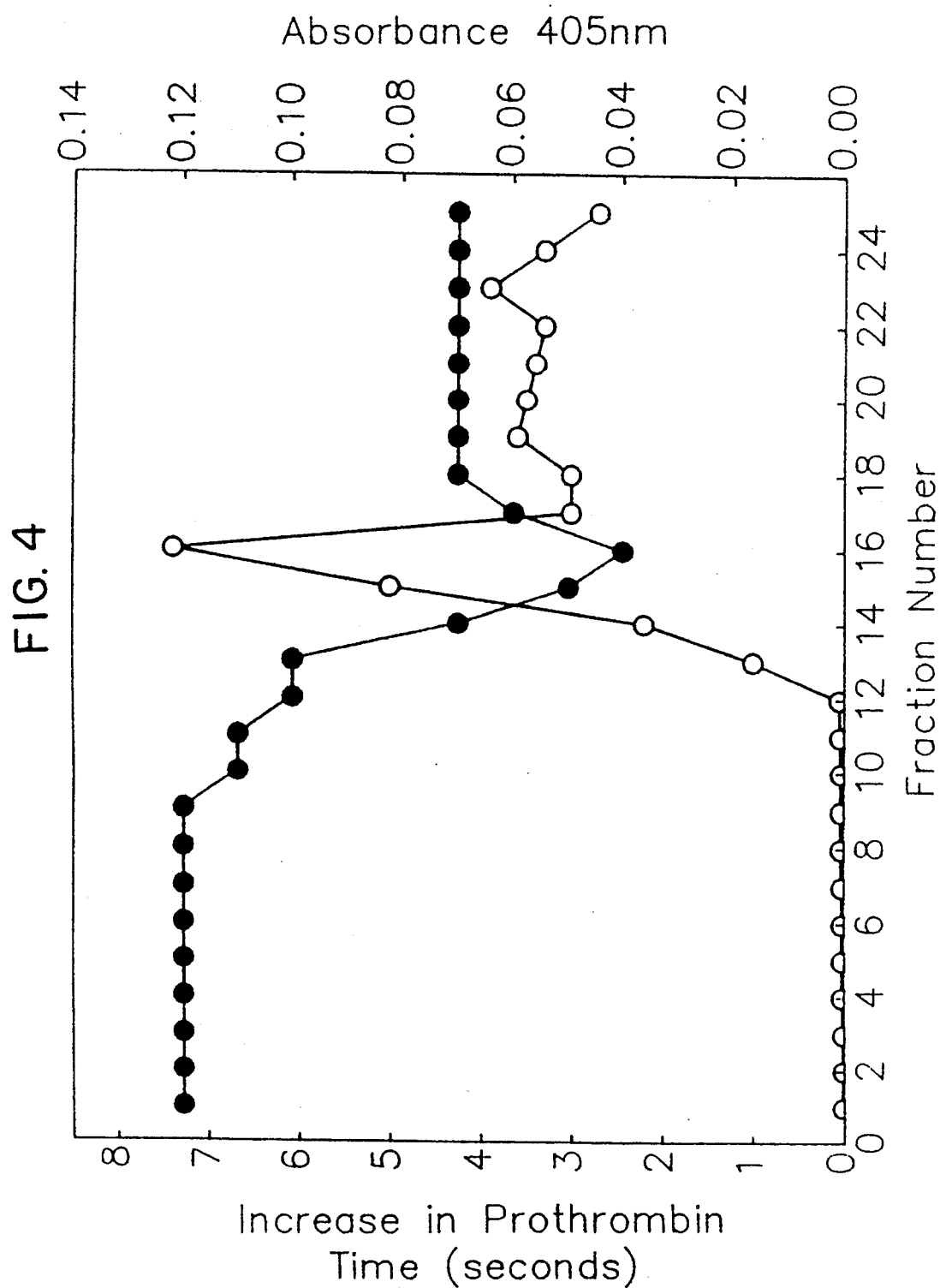
FIG. 4. Fractionation of the $FX_a$ inhibitor by affinity chromatography on bovine $FX_a$-Affi-Gel-15. Proteins were eluted from the column with 0.1M benzamidine. Flow rate was 4 ml/hour and 1.2 ml fractions were collected; 1/500 dilutions of the chromatographic fractions were assayed for anticoagulant (open circle) and anti-$FX_a$ (filled circle) activities as described.

Salivary gland extract containing 25 mg soluble protein in 4 ml of extraction buffer was applied to a DEAE-5PW (Waters Associates) anion exchange column (0.46×7.5 cm) equilibrated in 20 mM HEPES, pH 7.8 (Buffer A). Proteins were then eluted with a linear gradient of NaCl ranging from 100% Buffer A (initial conditions) to 100% Buffer B (Buffer A containing 0.5M NaCl) over 60 minutes. The flow rate was 1 ml/minute. The fractions eluting between 0.1–0.20M NaCl containing both anticoagulant and anti-FX$_a$ activities were pooled (see FIG. 2), diluted with Buffer A to a conductivity ≦10 mS/cm and then applied to a 0.5×5 cm heparin-agarose column (Bethesda Research Laboratories Life Technologies, Inc.). The further purification of the DEAE fractions with anticoagulant activity on heparin-agarose is shown in FIG. 3. The column was extensively washed with Buffer A and then eluted with a linear salt gradient; the gradient ranged from 100% Buffer A to 100% Buffer B (Buffer A+1M NaCl) over 75 minutes. The flow rate was 1 ml/minute. In some applications, the anti-FX$_a$ activity was recovered by fractionating the proteins over a column of bovine FX$_a$-Affi-Gel-15 (FIG. 4). Crude extracts or chromatographic fractions having anticoagulant activity were adjusted to 0.1% Tween-20 and fractionated by affinity chromatography on a column having a 2 ml bed volume of bovine FX$_a$-Affi-Gel-15. The column was extensively washed in 0.05M HEPES, 0.1M NaCl, pH 7.5 containing 0.1% Tween-20 and the proteins eluted with 0.05M HEPES, 0.1% Tween-20, pH 7.5 containing 0.1M benzamidine. Clot and amidolytic assays were performed on 1/500 dilutions of the collected fractions. The column was eluted at a flow rate of 4 ml/hour. Final fractionation of the anticoagulant and amidolytic activities was performed on a 2.1×30 mm Aquapore RP-300, C-18 reverse-phase column with the Applied Biosystems Model 130 protein/peptide separation system. Proteins were eluted with a linear gradient of acetonitrile; the gradient ranged from 100% Buffer A (0.1% trifluoroacetic acid in H$_2$O) to 100% Buffer B (0.07% trifluoroacetic acid/70% acetonitrile/29.93 % H$_2$O) over 40 minutes. Fractions (see FIG. 5) containing protein were dried overnight on a Savant speed vac system. Samples were redissolved in 0.1% trifluoroacetic acid/H$_2$O and various aliquots analyzed by SDS polyacrylamide gel electrophoresis, gas-phase microsequencing, amino acid analysis and for anticoagulant and amidolytic activities.

Analytical Polyacrylamide Gel Electrophoresis

Polyacrylamide gels (8×8 cm and 1 mm thick), 20% and 12% in acrylamide, containing a 3% stacking gel were placed in a Mighty Small electrophoresis unit (Hoefer Scientific Co.) and subjected to a constant current of 10 mA/gel. Gels contained 0.25M Tris-HCl, pH 9.0 and 0.1% sodium dodecyl sulfate (SDS). Electrophoresis was performed in 25 mM Tris-HCl, 0.2M glycine, 0.1% SDS, pH 8.4. Dried samples were solubilized in 35 μl of 10 mM Tris-HCl, pH 6.8, 1% SDS, 20% sucrose, 1 mM EDTA, 6M urea, 1% 2-mercaptoethanol and 0.03% bromophenol blue; prior to electrophoresis, samples were heated at 60° C. for 15 minutes. Gels were fixed and the proteins detected by the silver stain procedure of Oakley, et al, *Anal. Biochem.* 105, 361–363 (1980). Apparent molecular weights of proteins were determined by extrapolation from a standard plot of the logarithm of the molecular weights versus the electrophoretic mobility of standard proteins. The protein standards were phosphorylase B (98,000), bovine serum albumin (67,000) ovalbumin (43,000), carbonic anhydrase (30,000), soybean trypsin inhibitor (20,000), and α-lactalbumin (14,400).

Sequence Analysis

Automated Edman degradations were performed on a Model 470A protein-peptide sequencer (Applied Biosystems, Inc.) with reagents, instructions and standard programs supplied by the manufacturer. The phenylthio-hydantoin-derivitized amino acids were analyzed at each cycle on a Model 120 PTH-Analyzer (Applied Biosystems, Inc.) directly on-line with the 470A gas-phase sequencer.

Amino Acid Analysis

Autosampler microvials (Hewlett Packard), used as hydrolysis tubes, were sonicated in methanol then heated in a furnace at 500° C. for 4 hours. Peptides were hydrolyzed by gas-phase hydrolysis in a Picotag Workstation (Waters Associates) at 105° C. for 20 hours with 200 μl of constant boiling HCl (Pierce Chemical Co.) containing a few microliters of liquified phenol (MCB). Hydrolyzed samples were taken to dryness in a speed vac concentrator (Savant), dissolved in a small volume (typically 15–30 μl) of 0.1N HCl and placed in the autosampler of a Model 1090 HPLC (Hewlett Packard). Amino acid analysis was performed using the Aminoquant analyzer by Hewlett Packard in the high sensitivity configuration (fluorescence detection). Amino acids were determined after precolumn derivatization with first O-phthaladehyde (OPA) for primary amino acids and then 9-fluorenylmethyl chloroformate (FMOC) for secondary amino acids. Blankenship et al., *Anal. Biochem.* 178, 227–232 (1989). The derivatized amino acids were separated by reverse-phase HPLC with columns, reagents and instructions supplied by the manufacturer. This system accurately quantitates 1–500 pmoles of aminoacyl mass.

Figure 1B:
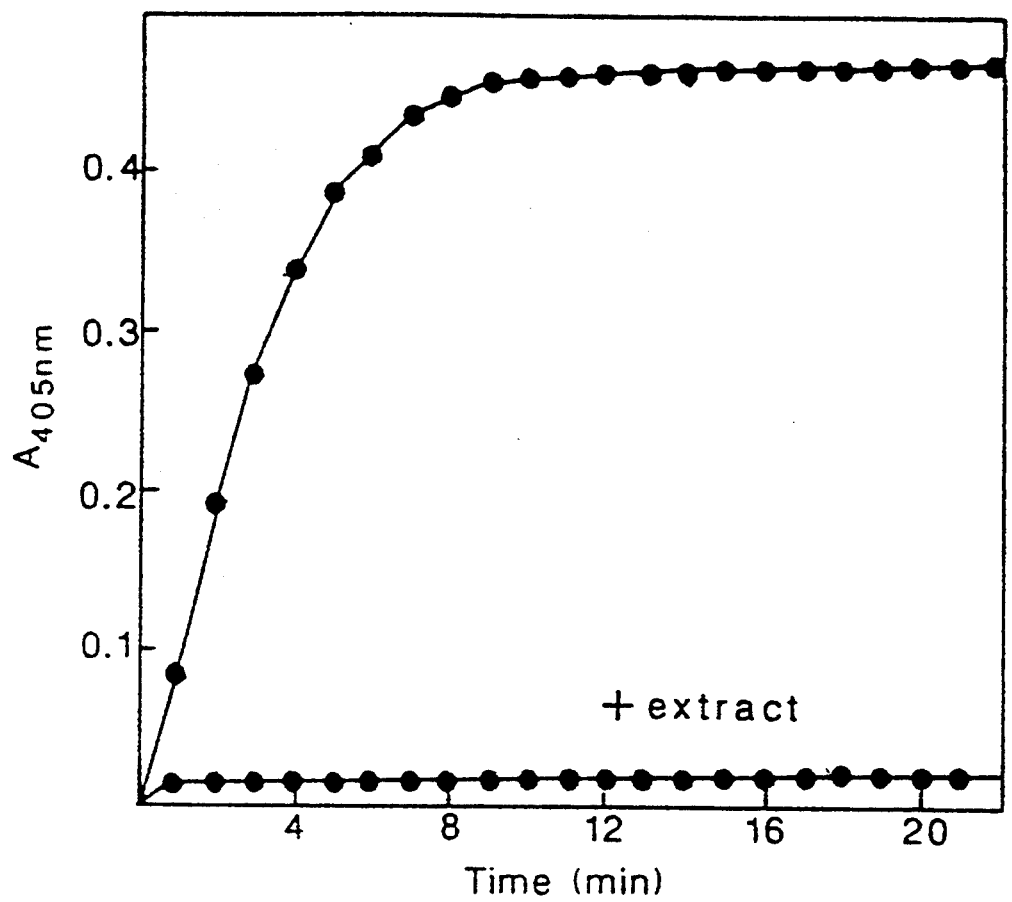

FIG. 1 shows the anti-$FX_a$ activity in crude salivary gland extracts of *H. ghilianii*. The active principle inhibits both human (see inset) and bovine $FX_a$ but not human and bovine thrombins (data now shown).

Figure 2A:
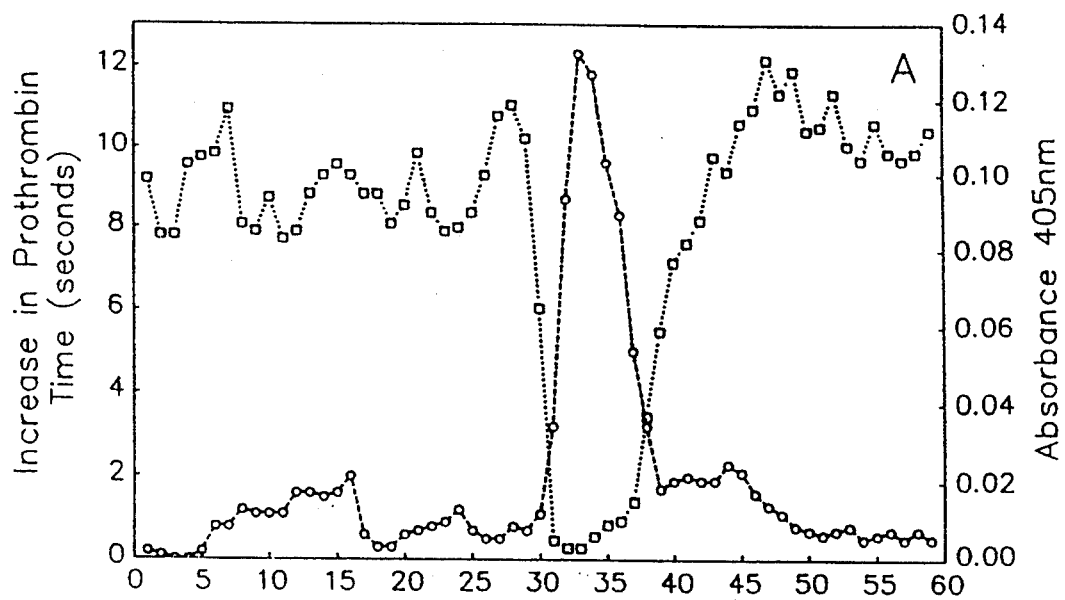
FIG. 2. Fractionation of crude salivary gland extract (25 mg soluble protein) on a 0.46×7.5 cm DEAE anion exchange column. Proteins were eluted with a linear gradient of NaCl in 20 mM HEPES, pH 7.8 (see methods for details). The flow rate was 1 ml/minute and 1 ml fractions were collected. Panel A: Anticoagulant activity (open circles) was determined by a one-stage clot assay as the prolongation in prothrombin time. Inhibition of $FX_a$ was measured at 405 nm for inhibition of p-nitroaniline formation (open squares) using the chromogenic substrate methoxycarbonyl-D-cyclohexylglycyl-glycyl-arginine-p-nitroaniline acetate. Panel B: This panel shows the *H. ghilianii* protein elution profile monitored by absorption at 280 nm. The fibrinogenolytic activity (hementin) is shown by the cross-hatched area. Hementin activity does not coelute with the anti-$FX_a$ or major anticoagulant activities.
Figure 2B:
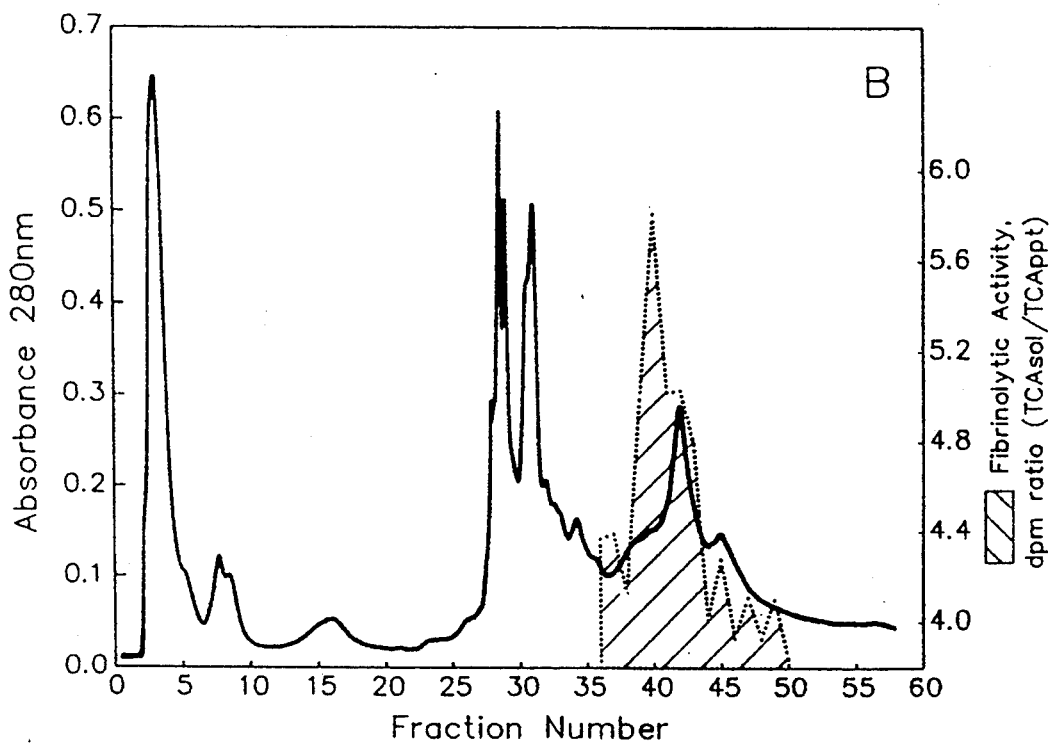

FIG. 2 shows the chromatography of 25 mg of the soluble protein extract by anion exchange on DEAE. The anticoagulant and $FX_a$ inhibitory activities coelute between 0.1–0.16M NaCl (panel A) between fractions 30–35. The fibrinogenolytic activity, without anti-$FX_a$ activity, eluted above 0.20M NaCl (panel B) between fractions 37–44 (hatched area). This material promoted clot (fibrin) lysis, degraded $^{125}$I-labeled fibrinogen (FIG. 2, Panel B) and was shown to degrade the α,β, and γ chains of purified fibrinogen by SDS-PAGE (not shown). The fibrin(ogen)olytic action of this fraction is attributable to hementin. Moreover, fractions with anti-FXa activity showed no fibrin(ogen)olytic activity. Based on the results of FIGS. 1 and 2, the inhibitor eluting between 0.1–0.16M NaCl is not due to hirudin of *Hirudo medicinalis* (J. Dodt, et al., *Biol Chem. Hoppe-Seyler* 36.6, 379–385 (1985)) or hementin, the fibrin(ogen)olytic component of *Haementeria ghilianii* (S. M. Malinconico, et al., *J. Lab. Clin. Med.* 103, 44–58 (1984)). As is shown in FIG. 2, 25 μl of the fractions having peak activity prolonged the prothrombin time by 16 seconds and completely inhibited 17 ng of $FX_a$ in the amidolytic assay. Based on the assays of the DEAE fractionated extract, the $FX_a$ inhibiting activity accounts for the major anticoagulant activity.

The anticoagulant fractions with anti-$FX_a$ activity from the DEAE column were pooled and then fractionated by heparin agarose chromatography (FIG. 3). Anticoagulant and anti-FXa amidolytic activities coeluted between 0.45–0.55M NaCl. Moreover, 25 μl of fractions showing peak anticoagulant activity prolonged the prothrombin time by ≈17 seconds and completely inhibited the hydrolysis of the chromogenic substrate by 16 ng of purified $FX_a$.

Fractionation of the anticoagulant/anti-$FX_a$ activities by affinity chromatography on $FX_a$-Affi-Gel-15 is shown in FIG. 4. The anticoagulant and anti-$FX_a$ activities were eluted together from the column with 0.1M benzamidine, a reversible active site serine protease inhibitor.

Figure 5A:
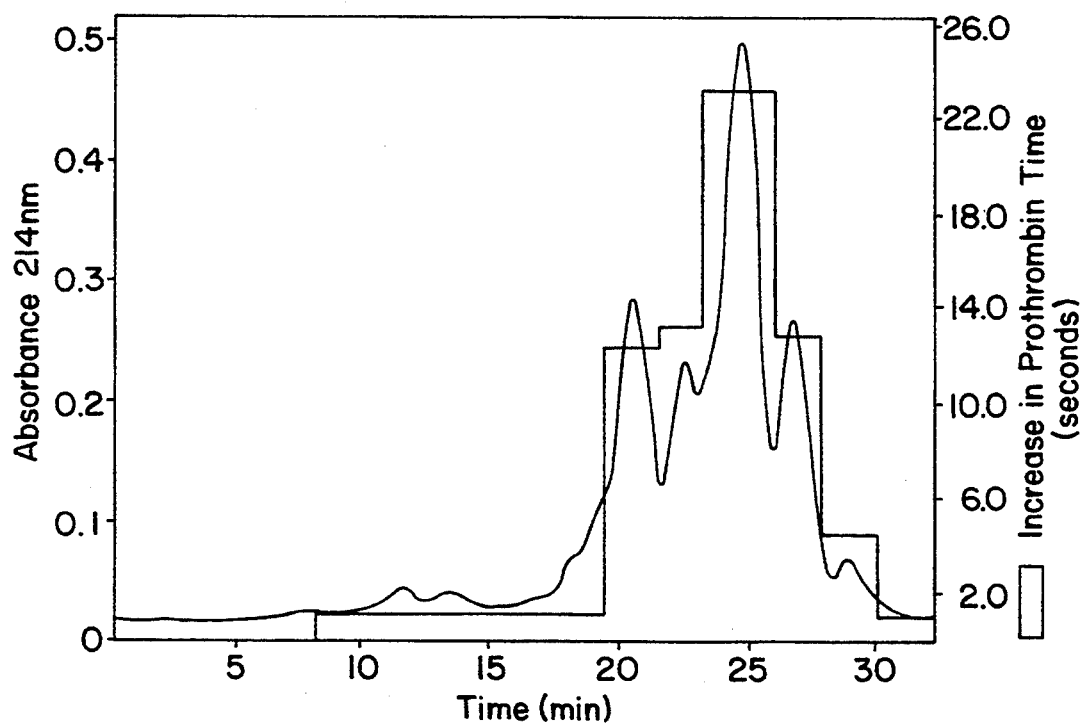
FIG. 5. Purification of the *H. ghilianii* anti-$FX_a$ principle(s) (ghilantens) by reverse-phase HPLC. Peak fractions with coeluting anticoagulant and anti-$FX_a$ activities described above were fractionated by microbore reverse-phase HPLC on a 2.1×30 mm Aquapore RP-300 column. The shaded area shows the anticoagulant acitivity distributed across the peak fractions. The inset shows the rechromatography of the initial reverse-phase separation on the same column. By rechromatography discrete, non-overlapping peaks were obtained. The major $FX_a$ inhibitory activities were found in ghilantens $P_4$ and $P_5$ (heavy shading); activity was also detected in ghilantens $P_1$, $P_2$ and $P_3$ (lighter shading).
Figure 5B:
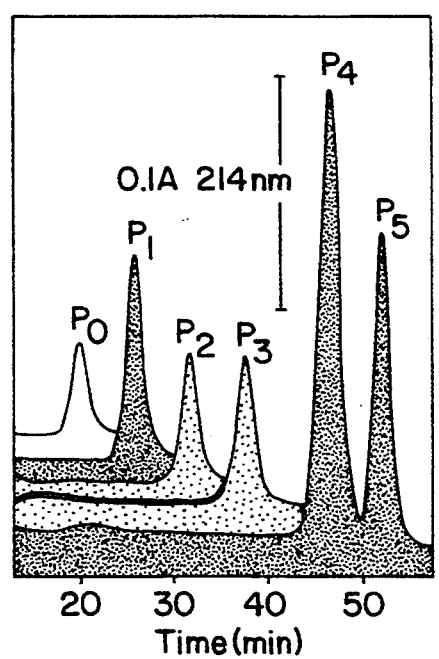

Further fractionation of the inhibitor by microbore reverse-phase HPLC is shown in FIG. 5. As can be seen, four minor and two major peaks were resolved with the anticoagulant activity distributed across the multiplet of peaks. Refractionation yielded six discrete peaks, designated $P_0$–$P_5$ (see inset). Of these, $P_4$ and $P_5$ showed the major anticoagulant and anti-$FX_a$ activities with $P_1$–$P_3$ also showing activity but present in lower abundance. No activity was detected in $P_0$.

Figure 6A:
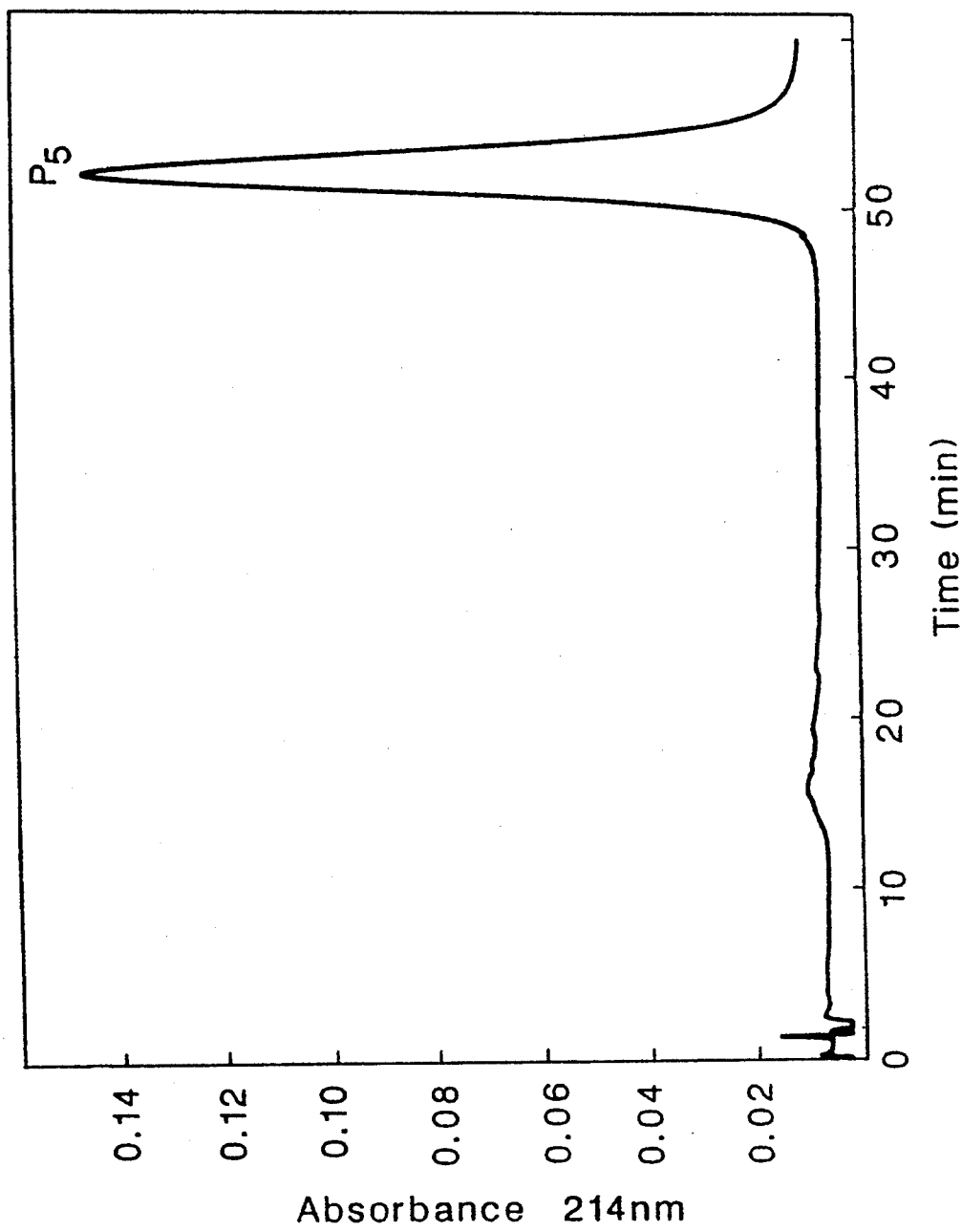
FIG. 6. Microbore reverse-phase HPLC of $P_5$. Absorbance was monitored at 214 nm for the *H. ghilianii* protein $P_5$. The inset shows a SDS PAGE (12% acrylamide) of $P_5$ isolated by microbore reverse-phase HPLC. Lane a shows the molecular weight standard proteins and lane b, purified $P_5$. Proteins were detected by silver stain according to the method of Oakley, et al., *Anal. Biochem.* 105: 361–363, (1980).
Figure 6B:
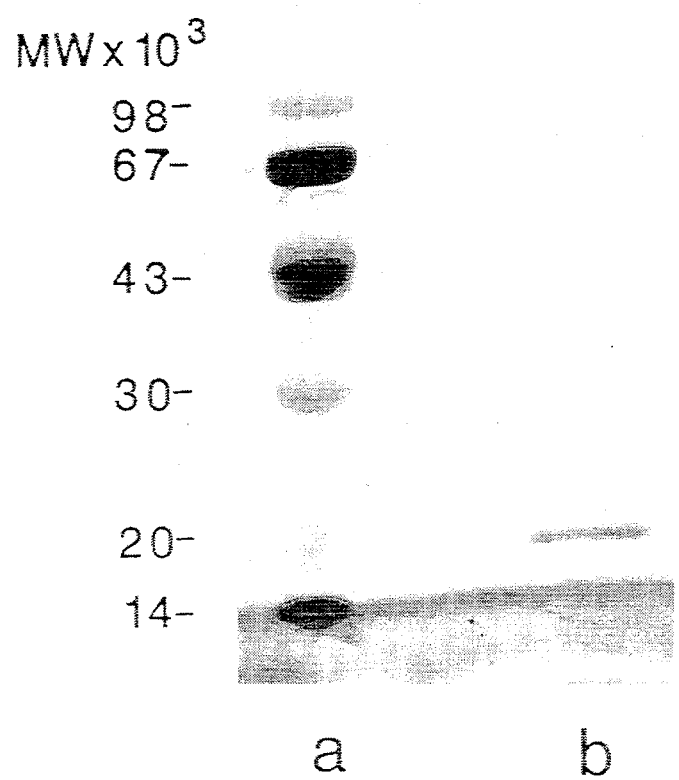

SDS PAGE (20% acrylamide) of fractions $P_1$–$P_5$ verified that these proteins have similar mobilities with apparent molecular weights ≈18,000 (not shown). FIG. 6 shows the chromatographic profile of $P_5$ on microbore reverse-phase HPLC. The inset shows a 12% SDS-PAGE (12% acrylamide) of $P_5$. This pure component has an apparent molecular weight of 18,000, i.e., the apparent molecular w.eight of the purified $FX_a$ inhibitor does not vary significantly with polyacrylamide gel concentration between 12% and 20% suggesting it is not highly glycosylated.

Figure 7A:
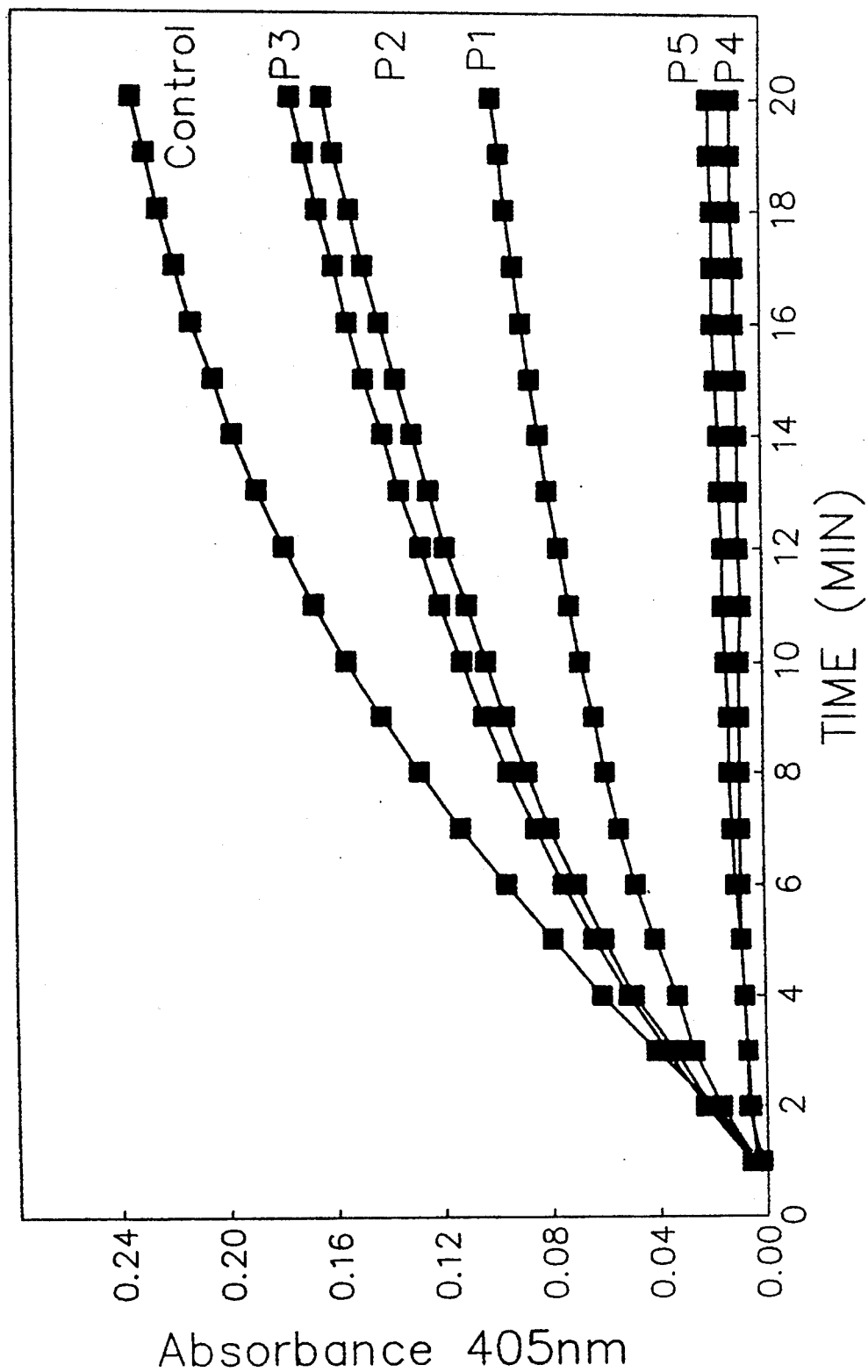
FIG. 7. Stoichiometric inhibition of $FX_a$ by *H. ghilianii* anticoagulant proteins $P_1$–$P_5$. Bovine factor $X_a$ (35 nM) was incubated with the indicated concentration of each inhibitor and the rate of p-nitroaniline formation from methoxycarbonyl-D-cyclohexylglycyl-glycyl-arginine-p-nitroanilide acetate was monitored at 405 nm as a function of time. The inhibitor and inhibited enzyme concentrations were: $[P_1]=24$ nM, $[FX_a]i=20$ nM; $[P_2]=16$ nM, $[FX_a]i=11$ nM; $[P_3]=14$ nM, $[FX_a]i=10$ nM; $[P_4]=60$ nM, $[FX_a]i=35$ nM; $[P_5]=40$ nM, $[FX_a]i=35$ nM. Inset: Dose-dependent inhibition of bovine factor $X_a$ by $P_5$.
Figure 7B:
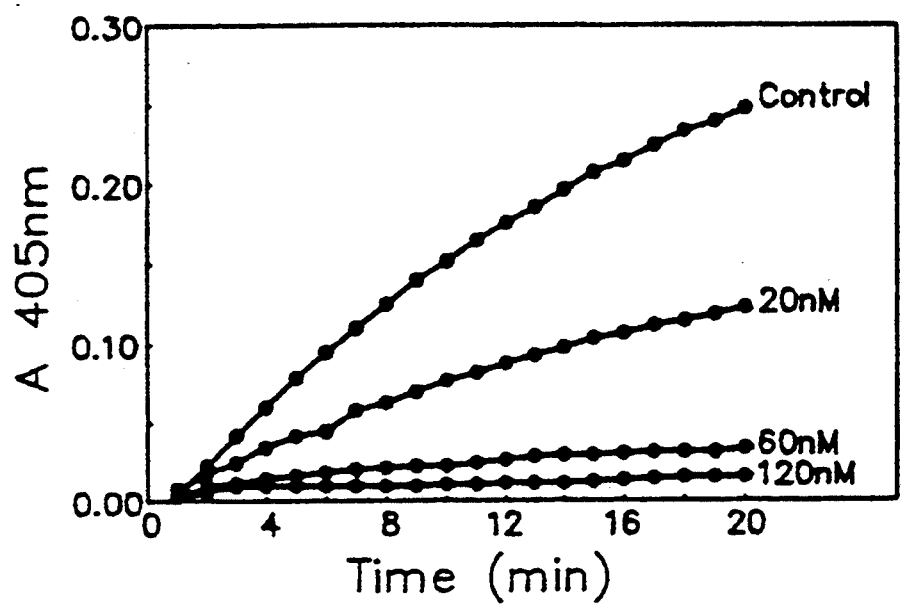
Figure 8A:
FIG. 8. Effect of recombinant-hirudin and *H. ghilianii* factor $X_a$ inhibitor proteins (ghilantens) on the metastatic spread of B16-F10 melanoma cells to the lungs of C57/BL mice.
Figure 8B:
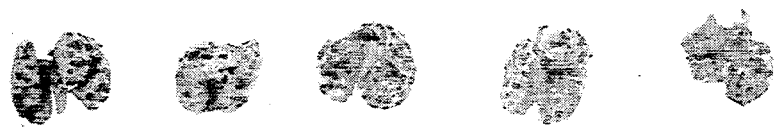
Figure 8C:
Figure 9A:
FIG. 9. Effect of higher dose ghilanten on the metastatic spread of B16F10 melanoma cells to the lungs of C57/BL mice. Control (C) received tumor cells only; V, vehicle (as defined in Table 1), received tumor cells only; ghilanten, same as control (left) and vehicle (right) but received 5 μg of ghilanten at −2, +2 and +4 hours relative to tumor cell innoculation.
Figure 9B:

FIG. 7 shows that each peptide gave >70% inhibition of factor $X_a$ at stoichiometric inhibitor concentrations indicating little difference in the specific activities of $P_1$–$P_5$. The dose-dependent inhibition of $FX_a$ by $P_5$ is shown in the inset with half-maximal inhibition at 20 nanomolar.

Table 3 shows the amino acid compositions of fractions $P_0$–$P_5$. The amino acid contents of $P_1$–$P_5$ were highly similar with respect to most residues with the exceptions that $P_4$ and $P_5$ showed slightly higher Asx, Glx, Lys and Pro. $P_0$ differed significantly from $P_1$–$P_5$ in its content of Asx, Glx, Thr, Arg, Val, Met, Ile, Lys and Pro. The similarity in compositions indicates that $P_1$–$P_5$ are sequence-related variants of the same protein.

TABLE 3

Amino Acid Analyses[a] of Fractions $P_0$–$P_5$ Obtained from Salivary Gland Extracts of *Haementeria Ghilianii* by Microbore Reverse-Phase HPLC

| Amino Acid | $P_5$ | $P_4$ | $P_3$ | $P_2$ | $P_1$ | $P_0$ |
|---|---|---|---|---|---|---|
| Asx | 9 | 9 | 7 | 8 | 8 | 6 |
| Glx | 11 | 13 | 9 | 9 | 10 | 7 |
| Ser | 5 | 5 | 4 | 4 | 4 | 3 |
| His | 1 | 1 | 1 | 1 | 1 | 1 |
| Gly | 7 | 9 | 7 | 7 | 7 | 5 |
| Thr | 5 | 5 | 5 | 5 | 5 | 4 |
| Ala | 3 | 3 | 3 | 3 | 3 | 3 |
| Arg | 9 | 10 | 9 | 10 | 10 | 6 |
| Tyr | 3 | 3 | 3 | 3 | 3 | 2 |
| Val | 4 | 4 | 3 | 3 | 3 | 2 |
| Met | 3 | 3 | 3 | 3 | 3 | 2 |
| Ile | 4 | 4 | 4 | 4 | 4 | 3 |
| Phe | 2 | 2 | 2 | 2 | 2 | 1 |
| Leu | 5 | 5 | 5 | 6 | 5 | 5 |
| Lys | 6 | 7 | 4 | 3 | 3 | 2 |
| Pro | 9 | 8 | 3 | 3 | 3 | 2 |

[a]Expressed as residues per mole of protein. Values were normalized to an Ala content of 3 residues/mole.

EXAMPLE 2

Amino Acid Sequence Determination
Pyridylethylation and Cyanogen Bromide Degradation The purified inhibitior was pyridylethylated according to the procedure of Freidman et al. *J. Biol. Chem.* 245:3868–3871 (1970), as modified by Hawke and Yuam, *Applied Biosystems Incorporated User Bulletin*, No. 28, (1987) for use with small amounts of protein. Briefly, dried protein ($\approx 1$ nanomole) was dissolved in 44 μl of 6M guanidine-HCl, 0.25M Tris-HCl, pH 8.5 and then sequentially reacted for 2 hours at room temperature with 3 μl of 10% β-mercaptoethanol and 3 μl of 4-vinylpyridine. The pyridylethylated protein was then desalted by microbore reverse-phase HPLC employing an Aquapore RP-300 column (2.1×30 mm) on an Applied Biosystems Inc. Model 130 protein-peptide separation system. The gradient was linear and ranged from 100% buffer A, (0.1% TFA in H$_2$O) to 100% buffer B, (0.085% TFA and 70% acetonitrile in H$_2$O) over 150 minutes at a flow rate of 100 μl/min. To produce fragments, the pyridylethylated protein ($\approx 1$ nanomole) was dissolved in 330 μl of 70% formic acid and several crystals of CNBr were added. The samples were then flushed with nitrogen, sealed and placed in the dark for 24 hours at room temperature. The samples were dried on a speedvac centrifuge (Savant), redissolved in 50 μl of 0.1% TFA in H$_2$O and repurified by microbore reverse phase HPLC using the same gradient as described above.

Enzymatic Digestions

Initial attempts to sequence the intact protein indicated a blocked amino (N—)terminus. The blocked N-terminal cyanogen bromide fragment was identified by its failure to sequence; amino acid analysis confirmed that sufficient peptide was present. Deblocking of the CNBR fragment was accomplished by incubating the peptide (3.6 μg) for 24 hours with pyroglutamate amino peptidase (sigma) in 40 μl of sodium phosphate buffer (pH 8.0) at an enzyme/substrate ratio of 1:10 (w/w). The reaction mixture was desalted by reverse-phase (RP) microbore HPLC and the deblocked CNBR fragment was sequenced for 20 cycles [CNBR-1(PYR)].

Limited tryptic digestion was performed on the intact protein prior to pyridylethylation. Anticoagulant protein (20 μg) was dissolved in 200 μl of 1% NH$_4$CO$_3$ (pH 9.00) and reacted with trypsin (Sigma-TPcK treated) for 24 hours at room temperature at an enzyme/substrate ratio of 1:20 (w/w). The reaction mixture was desalted by RP-microbore HPLC yielding a single peak. Subsequent reduction, pyridylethylation and rechromatography yielded four peaks, one of which yielded the 36 residue sequence TY-1 which overlapped sequence CNBR-2.

Amino Acid Sequence Analyses

Automated Edman degradations were performed on a Model 470A protein-peptide sequencer (Applied Biosystems, Inc.) with reagents, instructions and standard programs supplied by the manufacturer. The phenylthiohydantoin-derivatized amino acids were analyzed at each cycle on a model 120 PTH-analyzer (Applied Biosystems, Inc.) directly on-line with the 470A gas-phase sequencer.

N-TERMINAL SEQUENCE

⟵———— CNBR-1(PYR) ————⟶

(1) Gly Pro Phe Gly Pro Gly Cys Glu Glu Ala Gly Cys Pro Glu Gly Ser Ala Cys Asn Ile

INTERNAL SEQUENCES (2) Val Tyr Cys Ser His Gly Phe Gln Arg Ser Arg Tyr Gly Cys Glu Val Cys Arg Cys Arg Thr

⟵———————— TY-1 ————————

⟵——— CNBR-2 ———⟶

Glu Pro Met Lys Ala Thr Cys Asp Ile Ser Glu Cys Pro Glu Gly

————————⟶

⟵———————— CNBR-3 ————————

(3) Cys Ser Arg Leu Thr Asn Lys Cys Asp Cys Lys Ile Asp Ile Asn Cys Arg Lys Thr Cys

————⟶

Pro Asn Gly Leu Lys

We claim:

1. A method for inhibiting a melanomic tumor metastases in a patient in need thereof comprising administering an effective amount a peptide having substantially the sequence of:

Pyr-Glu-Gly-Pro-Phe-Gly-Pro-Gly-Cys-Glu-Glu-Ala-Gly-Cys-Pro-Glu-Gly-Ser-Ala-Cys-Asn-Ile-Ile-Thr-Asp-Arg-Cys-Thr-Cys-Pro-Glu-Val-Arg-Cys-Arg-Val-Tyr-Cys-Ser-His-Gly-Phe-Gln-Arg-Ser-Arg-Tyr -Gly-Cys-Glu-Val-Cys-Arg-Cys-Arg-Thr-Glu-Pro-Met-Lys-Ala-Thr-Cys-Asp-Ile-Ser-Glu-Cys-Pro-Glu-Gly-Met-Met-Cys-Ser-Arg-Leu-Thr-Asn-Lys-Cys-Asp-Cys-Lys-Ile-Asp-Ile-Asn-Cys-Arg-Lys-Thr-Cys-Pro-Asn-Gly-Leu-Lys-Arg-Asp-Lys-Leu-Gly-Cys-Glu-Tyr-Cys-Glu-Cys-Lys-Pro-Lys-Arg-Lys-Leu-Val-Pro-Arg-Leu-Ser;

or a pharmaceutically acceptable salt thereof.

2. A method according to claim 1 wherein the patient has lung cancer.

3. A method according to claim 1 wherein the daily dosage of the antimetastatic factor administered is from about 0.01 to about 2,000 mg/kg body weight.

4. A method according to claim 3 wherein the daily dosage administered is from 1 to about 200 mg/kg body weight.

5. A method according to claim 3 carried out in preparation for a surgical procedure to remove tumorous material.

6. A method according to claim 3 wherein the compound is administered promptly after the detection of the cancer.

* * * * *

UNITED STATES PATENT AND TRADEMARK OFFICE
CERTIFICATE OF CORRECTION

PATENT NO.   :   5,447,911

DATED        :   September 5, 1995

INVENTOR(s)  :   Alan D. Cardin and Sai Prasad Sunkara

It is certified that error appears in the above-identified patent and that said Letters Patent is hereby corrected as shown below:

Column 3, line 61 the patent reads "TEE" and should read --The--.

Column 4, line 67 the patent reads: "Set" and should read --Ser--.

Column 5, line 66 the patent reads: 'metas tases" and should read --metastases--.

Column 6, line 2 the patent reads: "GILANTEN" and should read --GHILANTEN--.

Column 12, line 3 the patent reads: "36.6," and should read --366,--.

Signed and Sealed this

Fifth Day of November, 1996

Attest:

BRUCE LEHMAN

*Attesting Officer*    *Commissioner of Patents and Trademarks*